(12) United States Patent
Segal

(10) Patent No.: US 8,708,971 B2
(45) Date of Patent: Apr. 29, 2014

(54) MEDICAMENT DISPENSING DEVICE

(76) Inventor: Eric Segal, North York (CA)

( * ) Notice: Subject to any disclaimer, the term of this patent is extended or adjusted under 35 U.S.C. 154(b) by 0 days.

(21) Appl. No.: 13/319,216

(22) PCT Filed: May 7, 2010

(86) PCT No.: PCT/CA2010/000694
§ 371 (c)(1),
(2), (4) Date: Nov. 7, 2011

(87) PCT Pub. No.: WO2010/127449
PCT Pub. Date: Nov. 11, 2010

(65) Prior Publication Data
US 2012/0059319 A1   Mar. 8, 2012

Related U.S. Application Data

(60) Provisional application No. 61/176,128, filed on May 7, 2009.

(51) Int. Cl.
*A61M 37/00*   (2006.01)
*A61M 5/00*   (2006.01)
*A61M 5/32*   (2006.01)

(52) U.S. Cl.
USPC ........... 604/209; 604/181; 604/187; 604/131; 604/197

(58) Field of Classification Search
CPC . A61M 5/14566; A61M 5/142; A61M 5/172; A61M 5/14244; A61M 5/14546; A61M 5/3129; A61M 5/31513; A61M 2005/206; A61M 5/14248; A61M 5/2033; A61M 5/24; A61M 5/31511; A61M 2005/3139; A61M 5/3135; A61M 5/3156; A61M 5/31581; A61M 5/31595; A61M 5/31551
USPC ......... 604/131, 181, 187, 192–198, 207–209, 604/151–155, 110, 137, 232, 136, 156, 138
See application file for complete search history.

(56) References Cited

U.S. PATENT DOCUMENTS

| | | | |
|---|---|---|---|
| 6,241,709 B1 | 6/2001 | Bechtold et al. | |
| 6,689,108 B2 * | 2/2004 | Lavi et al. | ..... 604/211 |
| 2003/0105430 A1 | 6/2003 | Lavi et al. | |

FOREIGN PATENT DOCUMENTS

| | | |
|---|---|---|
| EP | 1932558 | 6/2008 |
| GB | 2396298 A | 6/2004 |
| WO | 2005009515 | 2/2005 |

* cited by examiner

*Primary Examiner* — Bhisma Mehta
*Assistant Examiner* — Niyati D Shah

(57) ABSTRACT

A portable medicament dispensing device having a mechanism which is not susceptible to jamming for dispensing the medication to a user. The device employs a coupling for coupling the relative motion between reciprocating body members housing the ancillary components and a barrel plunger associated with the syringe. One embodiment provides a pivoting coupling whereas an alternate uses a rack and pinion system. The advantage of simplifying such mechanisms results in a structure which has smooth unencumbered motion with fewer parts to avoid mechanical jamming during use.

2 Claims, 7 Drawing Sheets

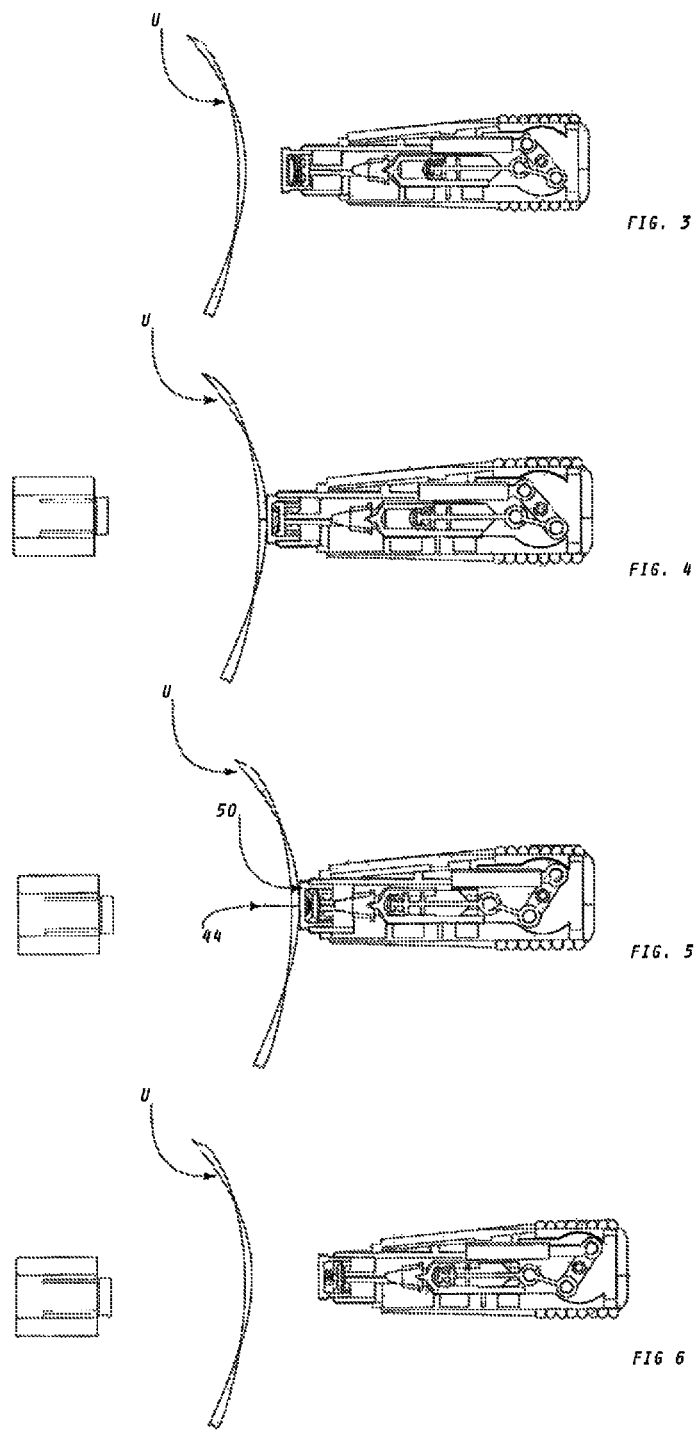

MEDICAMENT DISPENSING DEVICE

This application claims priority from U.S. Patent Application No. 61/176,128 filed May 7, 2009, the contents of which are incorporated herein.

TECHNICAL FIELD

The present invention relates to a medicament dispenser and more particularly, the present invention relates to a structure for dispensing a medicament where the structure has a mechanical coupling member to substantially reduce jamming of the components normally attributable to such devices.

BACKGROUND OF THE INVENTION

Single use single dose medicament delivery devices are widely known and are generally used to dispense medicaments such as epinephrine in an urgent manner to a user. The so called "epi pen" is a typical example of such arrangements. One of the significant disadvantages inherent with these devices relates to jamming. The existing devices often employ spring configurations for movement of key parts such as the needle as well as the barrel which assists in delivery of the medicament to the needle. In the scenario where a jam has occurred, the result can be fatal if the user cannot repair the device to function properly. In some instances, repair is impossible given urgent time constraints and the user is forced to dismantle or destroy the structure in order to gain access to the medication.

The above is possible where the user is not a child or a user otherwise not capable of achieving access. To address the limitations in the art, a variety of solutions have been advanced in the art. An example is provided in U.S. Pat. No. 6,808,507, issued Oct. 26, 2004, to Roser. In the arrangement discussed in this patent, a telescopic member is provided and a spring surrounds the needle. The arrangement is useful, however there is still a possibility that the spring could be defective or otherwise fail, thus complicating delivery.

Botich et al., in U.S. Pat. No. 6,039,713, issued Mar. 21, 2000, teach a pre-filled retractable needle device. The device, as is common with most arrangements, includes reciprocating body members, springs, etc. In this instance the device has a number of movable parts which elevates the possibility for jamming or failure.

U.S. Pat. No. 6,846,301, issued to Smith et al., Jun. 25, 2005, teach a disposable safety syringe with a vacuum system to withdraw the needle into the body after use. There is no provision for a mechanical linkage for quick delivery of the medicament.

Given the extent of development in the prior art, there exists a need for an improved medicament dispenser which is efficient and reliable while maintaining a lower profile than those devices currently available.

The present invention provides a significantly improved arrangement which is devoid of the structural limitations inherent with the prior art.

INDUSTRIAL APPLICABILITY

The technology set forth herein has utility in the medical arts inter alia.

DESCRIPTION OF THE INVENTION

One object of one embodiment of the present invention is to provide an improved medicament dispensing device.

An important objective of this invention is to provide an automatic injection device for dispensing a medicament, the device having a needle connected to a barrel adapted to retain medicament and a plunger within the barrel, characterized in that the device comprises:

a first body member and a second body member coaxially mounted for reciprocal movement, and housing the needle, the barrel and the plunger;

drive means connected between the first body member and the second body member for effecting the reciprocal movement; and coupling means on each of the first body member and the second body member coupled with the drive means, whereby upon reciprocal movement of the first body member and the second body member, the needle is exposed and the plunger is moved within the barrel for discharging the medicament.

In accordance with another object of one embodiment of the present invention, there is provided a method for dispensing a medicament from a device having a needle, connected to a barrel adapted to retain medicament and a plunger within the barrel, the device having a first body member and a second body member mounted thereon for reciprocal movement comprising the steps of:

providing a cover means for covering a tip of the needle;

positioning the device in contact adjacent a user's skin;

urging the device against the user to expose, in a first stage, the needle through the cover means; and urging, in a second stage, the device against the user to reciprocally move the cover means and the plunger where the needle penetrates a user's skin and the medicament is forced through the barrel and the needle to deliver the medicament to the user.

Having thus generally described the invention, reference will now be made to the accompanying drawings, illustrating preferred embodiments.

BRIEF DESCRIPTION OF THE DRAWINGS

FIGS. 3 through 6 are cross-sections of the device sequentially illustrating the components positions as the device is advanced through a pre-use position through to use and withdrawal;

Similar numerals used in the drawings denote similar elements.

BEST MODE FOR CARRYING OUT THE INVENTION

Figure 1:
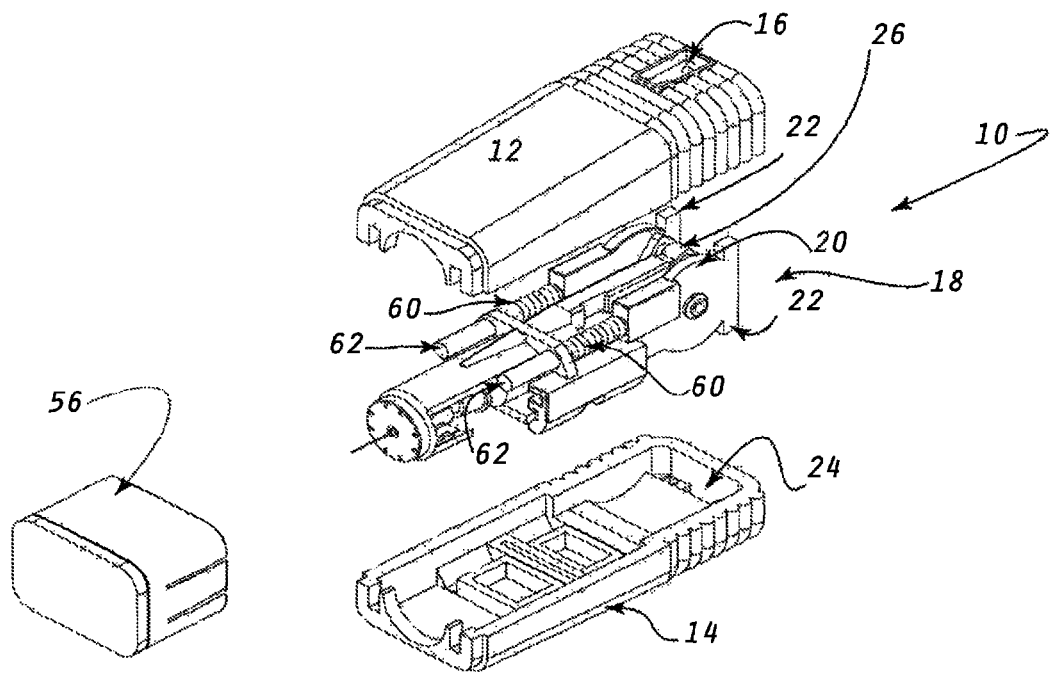
FIG. 1 is an exploded view of the arrangement according to one embodiment of the present invention.

Referring now to the drawings, FIG. 1 illustrates one embodiment of the present invention. The overall arrangement is denoted by numeral 10. The arrangement provides an exterior body, shown in the example in two sections 12 and 14. Section 12 provides an opening 16 to allow a user visibility of the interior to determine that the device has been discharged. This will be discussed in greater detail herein after.

Turning to the major components of the device, a second body member 18 is configured for reception and slidable movement with the exterior body supra. Member 18 has a mounting 20 with, as shown in the example, projections 22 configured for fixed location in seating 24 in body members 12 and 14. A drive member 26 is rotatably connected to mounting 20 and at one end thereof has a pivotally connected use indicator member 28 at pivot point 30 for indicating when the unit is used. The opposed end of member 26 pivotally connects coupling member 32 at pivot point 34. Member 32, at the opposed end thereof, has a pivotal connection 36. The connection at 36 is with a barrel plunger 38 received within barrel 40. Barrel 40 terminates in needle hilt 42 which, in turn, receives needle 44. As is illustrated, the barrel 40 retains a predetermined amount of medicament forwardly of plunger 38.

In order to provide protection and sterility to the device 10, the same includes a cover 46. The same is configured to always extend outwardly sufficiently to completely cover the tip of the needle. In this manner, springs 48 or other resilient means urge cover member 50 outwardly of a terminal end 52 of body 18. The cover member 50 also provides a foam cap 54 or other resilient material which protects the tip of the needle 44. This also assists in preventing spillage from the tip. As a further precaution and for adding durability and aesthetic appeal, a secondary cap 56 is frictionally retained by body members 12 and 14 at perimeter lip 58.

Figure 2:
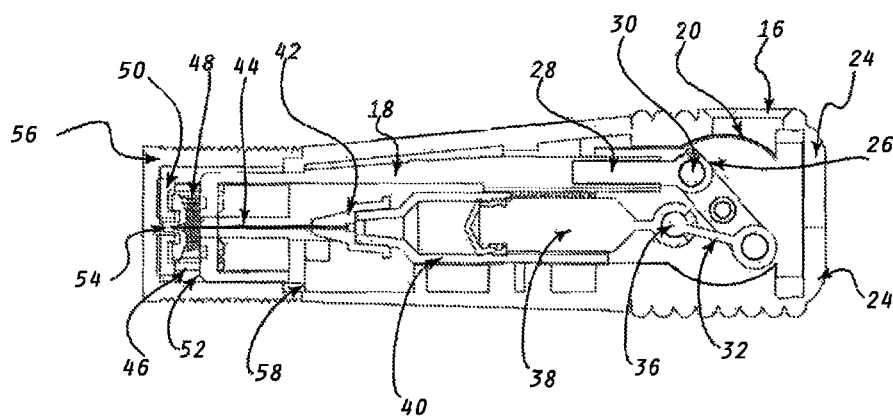
FIG. 2 is a cross-section of FIG. 1 with the arrangement shown in the ready to use state.

In order to bias the needle 44 in the position shown in FIG. 2, the storage or standby position, springs 59 are provided extending between mount 20 and spring retainers 62. FIG. 1 illustrates the springs in a compressed state.

With reference to FIGS. 3 through 6, shown are the various dispositions of the elements from a pre-injection position (FIG. 3) to a post injection position (FIG. 6).

FIG. 3 depicts the position of the elements in a relaxed, pre-injection state where the cover 50 is spaced from the user, U. In FIG. 4, first stage contact is made with the user, U. The cover 50 is forced backwardly toward terminal end 52, the springs 48 are compressed and the needle tip penetrates the foam cap 54 through to the skin of the user, U. In order to administer the medicament, the body formed by members 12 and 14 is urged forward to the position shown in FIG. 5. This movement results in the pivotal movement of coupling 32 by the motion of drive member 26. The coupling member 32 movement, in turn, by the pivotal connection, urges plunger 38 forward to discharge the medicament contained within barrel 40.

As will be realized from a review of FIGS. 4 and 5, once injection has been completed, indicator 28 extends rearwardly within the body to be visible within opening 16. This is indicative that the unit is used.

FIG. 6 illustrates the disposition of the components subsequent to an injection.

Figure 7:
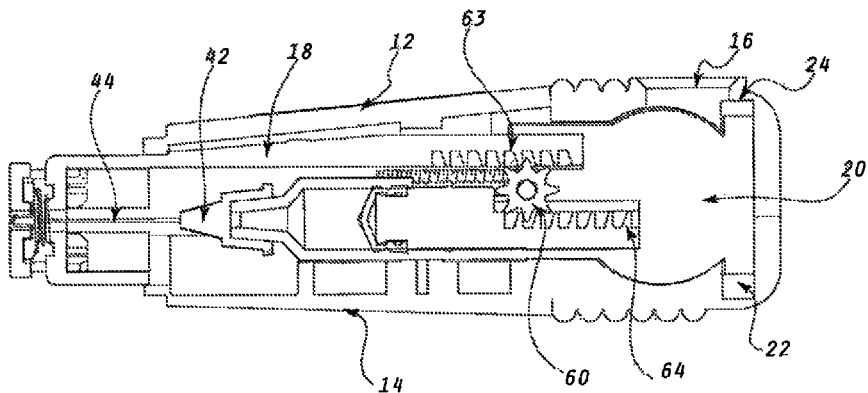
FIG. 7 is a cross-section of an alternate embodiment.

Turning now to FIG. 7, shown is a longitudinal cross section of an alternate embodiment of the device, In this embodiment, the drive member is a toothed pinion 61, rotatably mounted to mount 20. Cooperating with pinion 61 is a pair of opposed toothed racks 63 and 64. Pinion 61 is received by racks 63 and 64 in the same manner as a rack and pinion system used in an abundance of mechanical systems. In the embodiment shown, rack 63 is integral with body member 18, while rack 64 is integral with plunger 38. Relative movement between the first body member and the second is the same as that discussed supra with respect to the first embodiment. As is evinced in the Figure, rack 63 is disposed in advance of rack 64. This staggered relationship allows for free movement of the outer body (members 12 and 14) to advance plunger 38.

Figure 8:
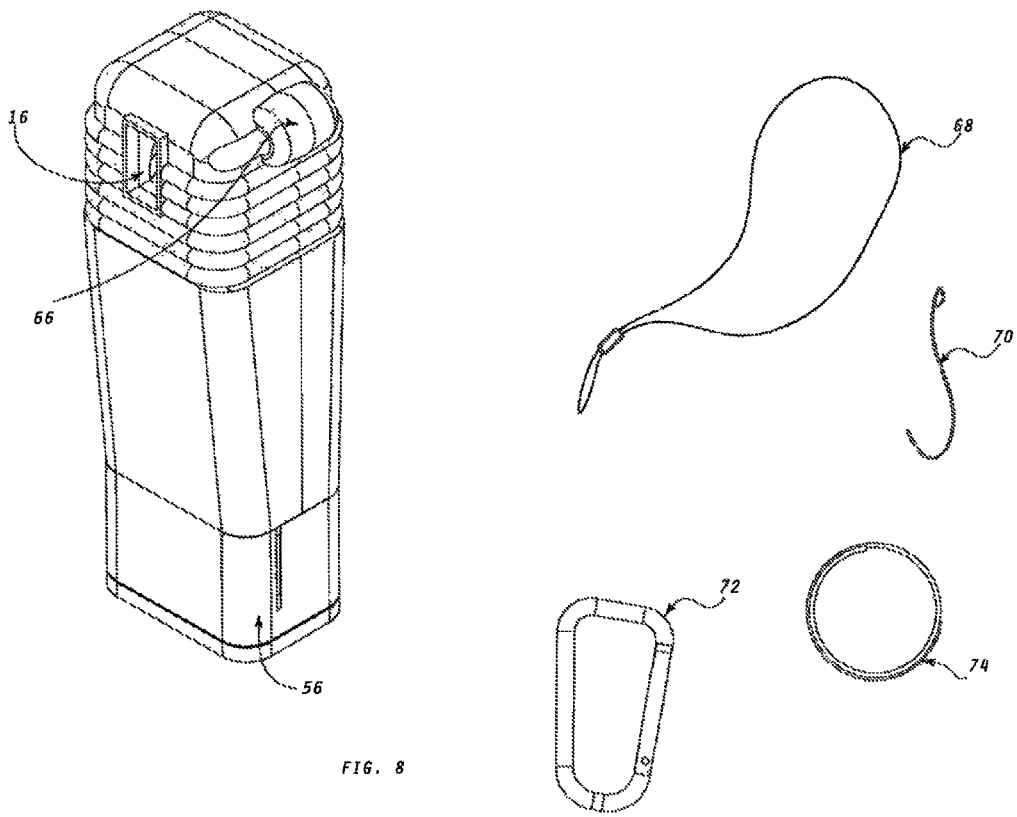
FIG. 8 is a perspective view of yet another embodiment.

FIG. 8 illustrates an embodiment of the device where an aperture 66 within the body is adapted to receive an elongate length 68, such as a lanyard, a hook 70, a clasp 72, a ring 74, etc. to allow for easier portability.

Figure 9:
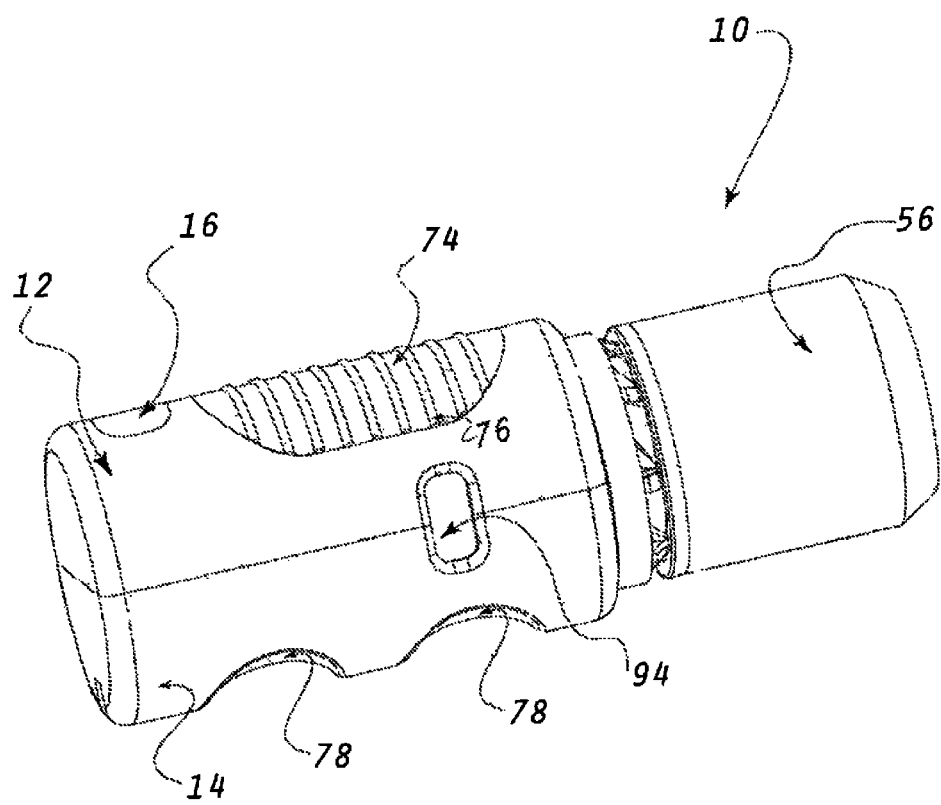
FIG. 9 is a perspective view of a further alternate embodiment of the present invention.

Referring now to FIG. 9, shown is a further embodiment of the present invention in an assembled state. The embodiment shown is generally similar to the embodiment that has been previously discussed, with this arrangement further including a top grip member 75 which, in the example, comprises a rubber material with a plurality of raised sections 76, which raised sections 76 are in spaced relation to provide, for example, a thumb rest for actuating the device. The material of which the top grip 75 may be made can include any material suitable for this purpose and may simply comprise the material of which the body members 12 and 14 are composed. In order to complement the use of the article, body 14 includes concavities 78, which concavities are useful to assist a user (not shown) in holding the device 10.

Figure 10:
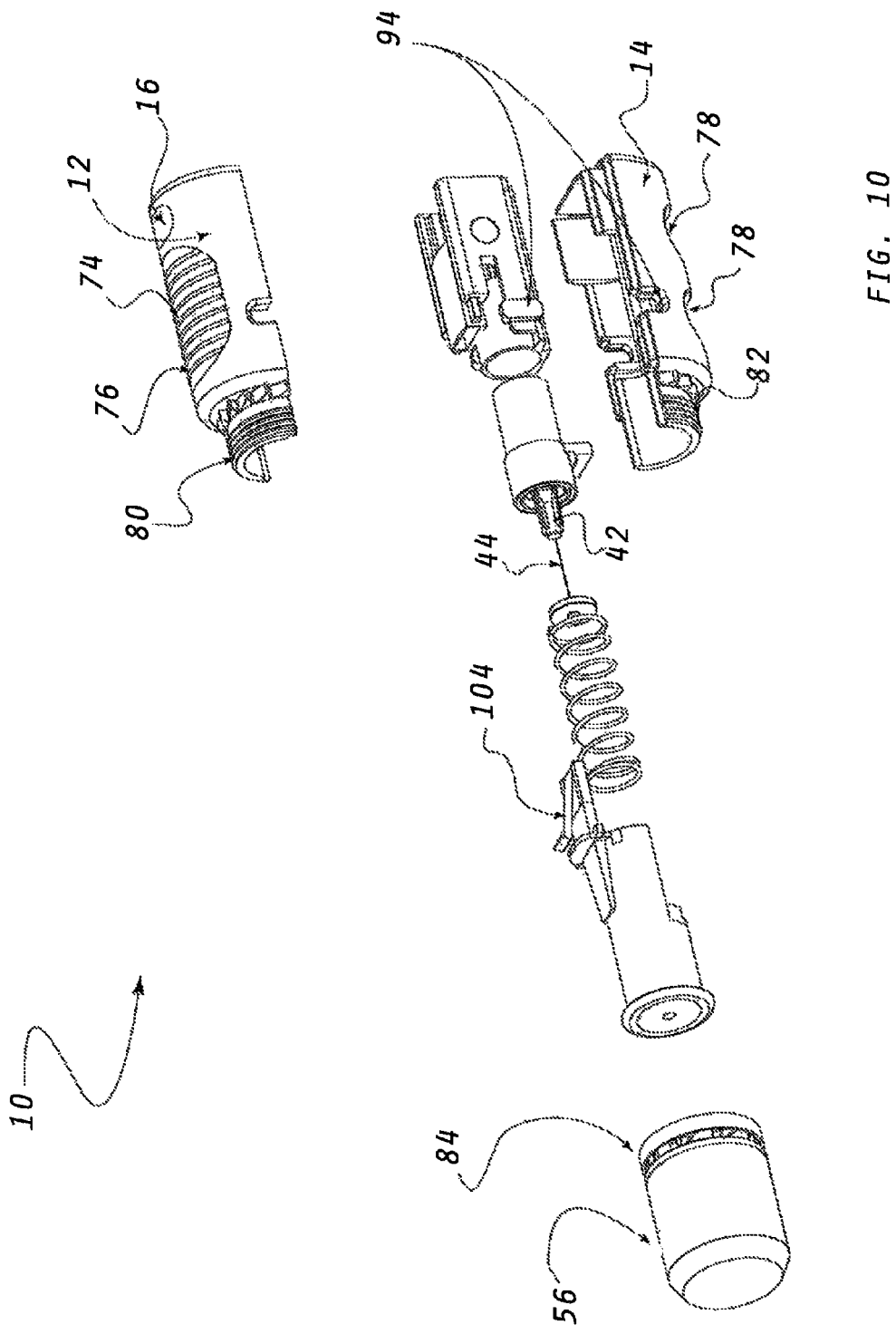
FIG. 10 is an exploded view of the device shown in FIG. 9.

Turning to FIG. 10, shown is an exploded view of the device shown generally in FIG. 9. Reference will be made to FIGS. 10 through 13 for the following description. In this embodiment, each of the body members 12 and 14 includes a threaded section 80 and 82, respectively. This is for purposes of engaging cap 56 which, in this embodiment is threaded (not shown) for purposes of engaging the threads 80 and 82. The cap 56 is of the variety that it is removable for a single use only. Such caps are known in the art. As a further security feature, the cap may include a breakaway seal 84 which typically takes the form of a ring attached to the body of the cap 56 by disengageable or breakaway connectors as is well known in the art.

As has been indicated previously, body members 12 and 14 are referred to collectively as a first body member, whereas the second body member 18, in this embodiment, includes a needle cover 88, which needle cover 88 substantially surrounds the entire needle and tip. At the terminal end of the needle 44 there is provided the foam cap 54 which accommodates the tip of the needle 44 which also cooperates with a cover member 88 to effectively surround and close the needle 44. This is obviously contributory to the hygiene and sterility of the device. Disposed coaxially about needle 44 and within the internal volume of cover there is disposed a spring 90 which is positioned between the needle cover 88 of member 86 and seating 92 within second body member 18 as shown. This retains the spring 90 until the device 10 is tended for use.

As is evident from FIGS. 10 through 13, the first body member formed by sub members 12 and 14 and the second body member 18 house the major components of the device and specifically, the plunger 38, barrel 40, needle hilt 42 and needle 44. As with the previous embodiments, second body member 18 includes the toothed rack coupling means 63, whereas the plunger 38 and more particularly, the arm of the plunger includes the second toothed rack coupling means 64. As with the previous embodiments, pinion 61 acts as a drive member which connects both of the racks 63 and 64. In this embodiment, observation window 94 is provided in the structure and visible through connected body members 12 and 14 to allow the user to determine whether barrel 40 contains any medicament and whether the medicament has been compromised.

Figure 11:
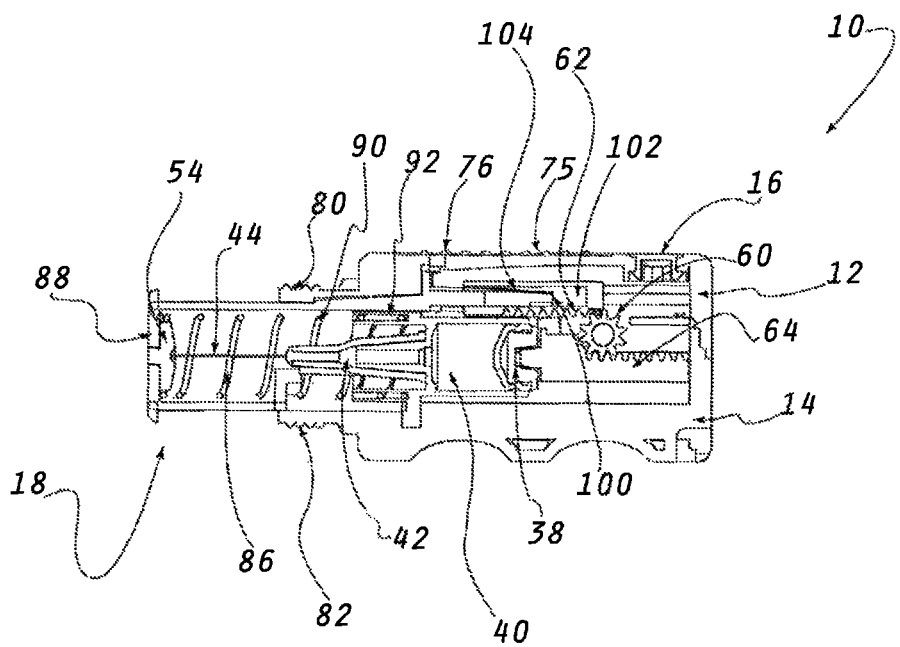
FIG. 11 is a longitudinal cross-section of the device before use.

This has been noted with respect to the previously described embodiments, in the embodiment shown in FIGS. 9 through 13, body members 12, 14 and second body member 18 are coaxially mounted and designed for reciprocal movement. As a particularly and beneficial advantage, in the embodiment shown in FIGS. 9 through 13 second body member 18, in opposition to the front cap 88 includes a terminal wall 100. As best seen in FIG. 11, terminal wall 100 is spaced from wall 102, which is formed by the connection of body members 12 and 14. This space permits movement of the body member 18 relative to assembled members 12 and 14 sufficiently to allow the needle 44 to penetrate cover 88 before injection. This avoids spillage and allows accurate injection of the medicament without wastage and allows for intramuscular injections.

Figure 13:
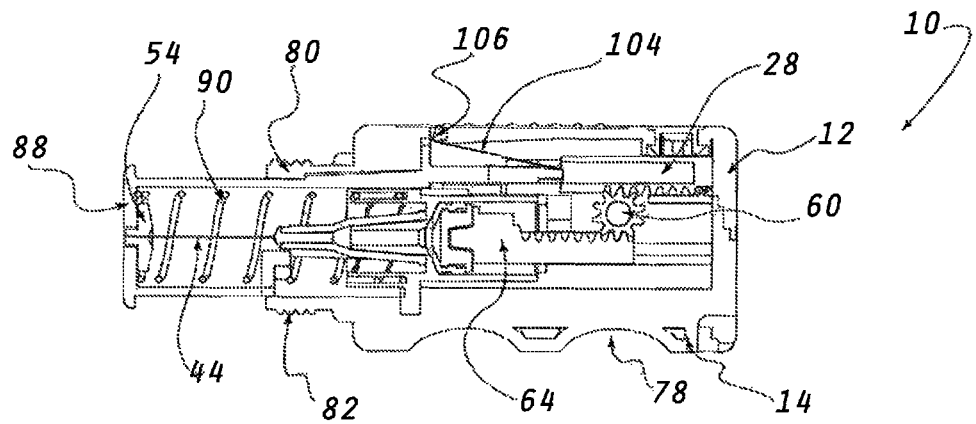
FIG. 13 is a longitudinal cross-section of the device in a post use position.

As a further attendant advantage, the embodiment under discussion also provides for a locking mechanism 104, shown in the example as a leaf spring and best shown in FIGS. 10 and 13. Spring 104, when the device is in a ready to use position is compressed by disposition of body members 12, 14 and 18 as illustrated in FIG. 11.

Figure 12:
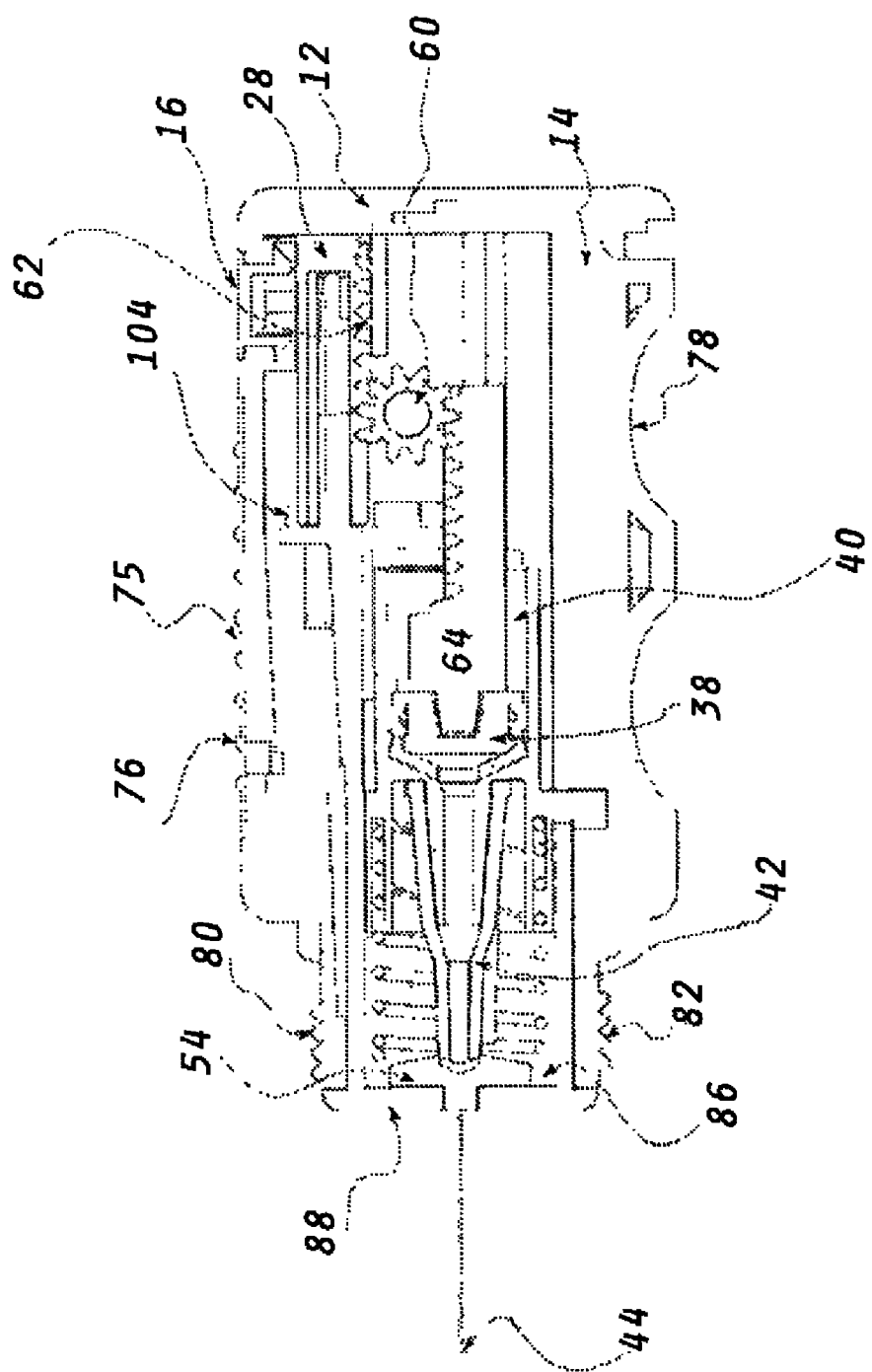
FIG. 12 is a longitudinal cross-section of the device in a use position.

Turning to FIG. 12, the device 10 is shown in an injection position where the needle 44 has penetrated the foam cap 54 and end cap 88 and where second body member 18 is retracted within the first body member composed of members 12 and 14. As is evident, the spring 90 is compressed, with the plunger 38 moved forwardly within the barrel 40 and with the rack 64 moved forwardly relative to the position shown in FIG. 11. In a similar manner, rack 63 is moved rearwardly as shown in FIG. 12. The locking member 104 is now compressed inside the gear rack 63 as shown in FIG. 12.

Turning now to FIG. 13, shown is a longitudinal cross-section of the device 10 subsequent to injection of the medicament. As is obvious from the illustration, once body member 18 is returned to the extended position with spring 90 relaxed, lock member 104 has nothing further to maintain a compressed state and therefore springs upwardly in a diagonal pattern as shown in FIG. 13, with the terminal end of 106 of spring 104 engaging the under surface of body member 14. This arrangement effectively locks retractable movement of body member 18 into the first body member 12, 14 whereby the device 10 cannot be reused. This is simply prevented by the lock arrangement 104. Further, as illustrated in FIG. 13, the second body member 18 fully extends to provide the cap 54 and end cap 88 to completely encapsulate and extend over the tip of needle 44 so that there is no possibility of inadvertent contact of the used needle with a user. As further benefit, as noted above with respect to the previous embodiments the opening 16 in body member 12 allows the user to determine whether the device has been discharged. A similar structure to that noted herein previously is provided for this benefit.

Other features of the device include:
the drive means may comprise an indirect drive;
the drive member is rotatably mounted to a support fixedly secured within the second body member;
the coupling means is connected to the drive member for pivotal motion relative thereto;
the coupling means is connected to the barrel for pivotal motion relative thereto; rotatable drive member includes stop means for limiting the movement between the first body member and the second body member;
device is a single use and single dose device;
the device includes indicator means for indicating when the device is discharged of the medicament;
the barrel and the first body member are mounted for coaxial movement in the same direction;
coupling means for coupling the rotatable drive member with the plunger, and the second body member;
a one time removable cap on the cover;
a break away security seal on the cap;
cover means for covering a tip portion of the needle;
a cap for releasable positioning over the cover means;
a retraction means for retracting the needle into the second body member subsequent to use;
springs mounted on the first body member as the retraction means;
springs for the cover means for urging the cover means back after use to cover the tip portion of the needle;
a section to allow for visibility of the indicator means; and
the first body member includes an aperture for receiving a member selected from the group consisting of an elongate length, a hook, a clasp and a ring.

The invention claimed is:

1. An automatic injection device for dispensing a medicament, said device having a needle connected to a barrel adapted to retain medicament and a plunger within said barrel, characterized in that said device comprises:
an outside first body member and a second body member coaxially mounted for reciprocal movement within said outside first body member, said outside body member housing said needle, said barrel and said plunger;
pinion means within said outside first body member and between said second body member and said plunger for effecting reciprocal movement of said second body member and said plunger; and
a first rack and a second rack housed within said outside first body member, said first rack connected to said second body member and said second rack connected to said plunger, each of said first rack and said second rack being coupled with said pinion means, whereby upon movement of said second body member reciprocal movement of said plunger is effected and said needle is exposed, in a position for discharging said medicament.

2. The automatic injection device as set forth in claim 1, wherein said second body member includes a needle cover for surrounding and covering said needle.

* * * * *